(12) United States Patent
Fausset et al.

(10) Patent No.: US 6,827,898 B1
(45) Date of Patent: Dec. 7, 2004

(54) HYPERTHERMIA METHOD AND APPARATUS

(75) Inventors: Michael Fausset, Lafayette, IN (US); Glenn Keeling, McMurray, PA (US); Marc G. Clupper, Hampstead, NC (US); Brad Rainier, Noblesville, IN (US)

(73) Assignee: ViaCirq, Inc., Canonsburg, PA (US)

( * ) Notice: Subject to any disclaimer, the term of this patent is extended or adjusted under 35 U.S.C. 154(b) by 0 days.

(21) Appl. No.: 09/979,640

(22) PCT Filed: May 25, 2000

(86) PCT No.: PCT/US00/14442

§ 371 (c)(1),
(2), (4) Date: Feb. 26, 2002

(87) PCT Pub. No.: WO00/71072

PCT Pub. Date: Nov. 30, 2000

Related U.S. Application Data

(63) Continuation-in-part of application No. 09/318,420, filed on May 25, 1999, now Pat. No. 6,579,496.
(60) Provisional application No. 60/180,563, filed on Feb. 4, 2000.

(51) Int. Cl.[7] .................. A61M 1/14; A61M 37/00; A61F 7/00
(52) U.S. Cl. .................. 422/46; 422/44; 604/4.01; 604/6.11; 604/6.13; 607/106
(58) Field of Search .................. 604/4.01, 6.01, 604/6.09, 6.11, 6.1, 6.13, 6.16, 19, 27, 30, 31, 65–67, 113, 114, 122, 123, 131, 151, 167.01, 167.03–167.06, 523, 264; 422/44, 46, 82.12–82.13, 105, 107–9, 113; 601/3; 606/27; 607/104–6, 107, 108–114; 417/15, 18, 20, 22; 165/200, 201, 279, 281–83, 287–88, 296; 210/634, 739, 741, 742, 767, 85, 87, 90, 175–6, 181, 252, 348, 416.1, 502.1

(56) References Cited

U.S. PATENT DOCUMENTS 2,886,771 A   5/1959   Vincent
3,482,575 A   12/1969  Claff et al.

(List continued on next page.)

OTHER PUBLICATIONS

DeMoss, et al., "Hyperthermia in the Treatment of Cancer", The Journal of Extra Corporeal Technology, vol. 17, No. 1, pp. 37–43, 1985.

(List continued on next page.)

*Primary Examiner*—Patricia Bianco
(74) *Attorney, Agent, or Firm*—Diederiks & Whitelaw, PLC

(57) ABSTRACT

A method and device for extracorporeal treatment of a patient by heating the patient's blood and/or a regional anatomic area which utilizes an optional hemodialysis machine capable of heating the fluids to 48° C., an optional parallel plate dialyzer together with a sorbent-based detoxifier, a tubular heat exchanger and a high flow positive displacement puma-in addition to various probes and catheters. The present invention also includes a disposable tubing set for directing fluids used in extracorporeal hyperthermia procedures. The tubing set contains a fluid reservoir, accommodates the positive displacement pump, and includes a heat exchanger for heating blood or fluid. The specific improvements in extracorporeal heating afforded by this system inhere in the combined high flow of the pump and the high temperature—up to 52° C.—achievable in the heat exchanger, which together provide unprecedented speed and efficiency in the administration of hyperthermia treatments in extracorporeal blood or circuits. Computer controlled alarms provide enhanced safety monitoring. The prepackaged sterilized fluid handling system enhances safety and may be configured to respond to a particular indication.

14 Claims, 3 Drawing Sheets

U.S. PATENT DOCUMENTS

| | | | |
|---|---|---|---|
| 4,061,141 A | | 12/1977 | Hyden et al. |
| 4,191,182 A | | 3/1980 | Popovich et al. |
| 4,321,918 A | | 3/1982 | Clark, II |
| 4,322,275 A | | 3/1982 | Jain |
| 4,381,004 A | | 4/1983 | Babb |
| 4,479,798 A | | 10/1984 | Parks |
| 4,540,401 A | | 9/1985 | Marten |
| 4,563,170 A | | 1/1986 | Aigner |
| 4,576,143 A | | 3/1986 | Clark, III |
| 4,632,125 A | * | 12/1986 | Webler et al. ............... 600/505 |
| 4,692,188 A | | 9/1987 | Ober et al. |
| 4,950,225 A | | 8/1990 | Davidner et al. |
| 5,092,836 A | | 3/1992 | Polaschegg |
| 5,354,277 A | | 10/1994 | Guzman et al. |
| 5,368,555 A | | 11/1994 | Sussman et al. |
| 5,391,142 A | * | 2/1995 | Sites et al. ................. 604/6.13 |
| 5,460,490 A | | 10/1995 | Carr et al. |
| 5,476,444 A | * | 12/1995 | Keeling et al. ............ 604/6.13 |
| 5,540,653 A | * | 7/1996 | Schock et al. ................ 604/7 |
| 5,730,720 A | * | 3/1998 | Sites et al. .................... 604/27 |
| 5,817,043 A | | 10/1998 | Utterberg |
| 5,871,526 A | | 2/1999 | Gibbs et al. |
| 5,989,238 A | | 11/1999 | Ginsburg |
| 6,156,007 A | | 12/2000 | Ash |
| 6,579,496 B1 | * | 6/2003 | Fausset et al. ................ 422/44 |

OTHER PUBLICATIONS

Yatvin, "An Approach to AIDS Therapy Using Hyperthermia and Membrane Modification", Medical Hypotheses, pp. 163–165, 1988.

Weatherburn, "Hyperthermia and AIDS Treatment [letter]", The British Journal of Radiology, vol. 61, No. 729, pp. 862–863, 1988.

Levin et al., "Whole Body Hyperthermia Experience in Breast Cancer at American International Hospital", Consensus on Hyperthermia for the 1990s, pp. 387–391, 1990.

Sanchez et al., "Overview of Whole Body Hyperthermia Experience at American International Hospital", Consensus on Hyperthermia for the 1990s, pp. 203–208, 1990.

James, "Hyperthermia Report: Only One Patient", AIDS Treatment News, Issue No. 104, pp. 1–2, 1990.

O'Malley, "Hyperthermia: Perfusion's Answer to AIDS?", Perfusion Life, pp. 5–13, 1991.

Perez et al., "Randomized Phase III Study Comparing Irradiation and Hyperthermia with Irradiation Alone in Superficial Measurable Tumors", Am. J. Clin. Oncol. (CCT) 14(2), pp. 133–141, 1991.

Logan, Jr. et al., "Total Body Hyperthermia in the Treatment of Kaposi's Sarcoma in an HIV Positive Patient", Med. Oncol. & Tumor Pharmacother, vol. 8, No. 1, pp. 45–47, 1991.

* cited by examiner

HYPERTHERMIA METHOD AND APPARATUS

The present application constitutes a National Stage filing under 35 U.S.C. § 371 of PCT/US00/14442 filed May 25, 2000 which is the continuation-in-part of U.S. application Ser. No. 09/318,420 filed May 25, 1999, now U.S. Pat. No. 6,579,496, and claims the benefit of U.S. Provisional Patent Application Ser. No. 60/180,563 filed Feb. 4, 2000.

FIELD OF THE INVENTION

The present invention relates to a specialized method and to disposable units for the circulation of fluids for perfusion-induced hyperthermia, including extracorporeal blood heating and sorbent-based detoxification, as an antiviral and antineoplasm protocol.

BACKGROUND OF THE INVENTION

Hyperthermia as a treatment of tumors has been carefully studied and applied since the 1960s. Prior to that time there were multiple reports of tumor regression coincident with febrile episodes. Subsequent analysis revealed that temperatures greater than 41° C. are ordinarily needed to induce tumor necrosis (tumor death). Although there are multiple methods of inducing hyperthermia by either direct skin contact or radiant heating, many physicians now favor an extracorporeal heat exchange (blood) circuit to raise patient temperatures. Others favor heating body cavities, such as the peritoneal cavity, with heated fluids to create hyperthermia of the tissue surfaces within the cavity. Patients may be maintained at 41.5° to 42° C. (rectal a) temperature) for three to four hours without severe cardiovascular compromise, although others report elevation of serum transaminases and bilirubin in patients kept at these temperatures for greater than 10 to 40 minutes. Instances of neurologic damage have been reported in association with serum hypophosphatemia, although no significant problems occurred once phosphate levels were maintained. Deaths have also been reported in two patients receiving hyperthermia at 41.5° to 42° C. for 1-½ to 2hours, presumably from massive liver tumor necrosis.

DeMoss, J. L. et al., "Hyperthermia in the Treatment of Cancer," The Journal of Extra-Corporeal Technology, Volume 17,No. 1, pp. 37–43, 1985, explains that tumors are vulnerable to heat and that the goal of hyperthermiic treatment therapy is to achieve cytotoxic temperatures in the tumor for a sufficient length of time without damaging the surrounding normal tissue. The rate at which blood flows through any given area of tissue determines the amount of heat that may be carried away and therefore is a major determinant of the temperature rise in that tissue. In normal tissue, heat causes vasodilation. In a tumor, the microvasculature is made up of an overabundance of capillary beds which are unable to dilate. Blood flow through the area is thus more sluggish and commensurately unable to dissipate heat applied to the area. The inability to respond to heat by dilation, as normal vasculature would, also subjects the tumor to hypoxia, anaerobic metabolism and local acidosis, and these conditions in turn make the tumor tissue more vulnerable to thermal injury.

Other literature addressing the utility of hyperthermia in the treatment of malignancy includes: Sanchez, R., "Overview of Whole Body Hyperthermia Experience at American International Hospital," Consensus on Hyperthermia for the 1990s, Plenum Press, New York, pp. 203–208 (1990); Levin, R. D. et al., "Whole Body Hyperthermia Experience in Breast Cancer at American International Hospital," Consensus on Hyperthermia for the 1990s Plenum Press, New York, pp.387–391 (1990); Perez, C. A. et al., "Randomized Phase III Study Comparing Irradiation and Hyperthermia with Irradiation Alone in Superficial Measurable Tumors," Am. J. Clin. Oncol. Vol. 14, No. 2, pp. 133–141 (1991); and others.

Patents relating to methods for the extracorporeal treatment of blood for cancers, viruses and parasites include U.S. Pat. No. 2,886,771 to Vincent, No. 3,482,575 to Claff, No.4,061,141 to Hyden, No.4,191,182 to Popovich, No.4,321,918 to Clark, No. 4,322,275 to Jain, No. 4,381,004 to Babb, No. 4,479,798 to Parks, No. 4,540,401 to Marten, No.4,563,170 to Aigner, No.4,576,143 to Clark and No.4,692,188 to Troutner et al.

There were two reasons for exploring the use of hyperthermia as a treatment for viral-associated neoplasms when such work began a few years ago. First, hyperthermia was known to have caused tumor regression in both animal and in human sarcomas. Studies on the biochemical and physiologic effects of hyperthermia had shown that damage to microvasculature is important for tissue necrosis associated with heat Second, the human lymphadenopathy associated virus was known to be heat-sensitive. McDougal et al. incubated lymphadenopathy associated virus at temperatures ranging from 37° to 60° C. and found the log kill followed first order kinetics. Thermal inactivation was decreased when the virus was in the lyophilized state compared to the liquid state (10-fold loss in LD50 121 seconds at 56° C. for virus in media versus 32 minutes in lyophilized state). It was also found that lymphadenopathy virus was 40% inactivated after 30 minutes in a 42° water bath, and 100% inactivated after the same time period at 56° C. Thus, hyperthermia can benefit patients suffering from viral infections in two ways. First, the hyperthermia kills malignant cells in the viral-associated neoplasms. Second, the hyperthermia directly inactivates the viruses themselves by denaturing them.

Studies have previously been completed in which whole body hyperthermia, achieved via extracorporeal circulation and thermoregulation, was used to treat Kaposi's Sarcoma associated with human immunodeficiency virus infection. While evaluation of the therapeutic effects of such treatment was the primary purpose of these studies, the simultaneous effects on HIV (human immunodeficiency virus) disease were evaluated by studying immunologic and virologic parameters of HIV infection as well as immunologic parameters related to Kaposi's Sarcoma In fact, the use of hyperthennia in AIDS (acquired inmmunodeficiency syndrome) patients with Kaposi's Sarcoma has received considerable public and media attention. The first two patients upon whom this procedure was performed were patients of the Atlanta pathologist Dr. Kenneth Alonso. Dr. Alonso initiated this experimental use of hyperthernia with Dr. William Logan, Jr., an Atlanta surgeon, as a pilot project to examine the possible use of this technique in the treatment of HIV associated diseases. Subsequently, Dr. Alonso requested that the National Institute of Allergy and Infectious Fri Diseases (NLAID) evaluate the study techniques, results and patients.

As reported in O'Malley, S., "Hyperthernia: Perfusion's Answer . . . ?", Perfusion Life, January 1991, pp. 6–13, a patient named Carl Crawford experienced a dramatic recovery from head-to-toe skin cancers after being treated with extracorporeal blood heating. (This case study was published in Logan, W. D. et al., "Case Report: Total Body Hyperthermia in the Treatment of Kaposi's Sarcoma.," Med. Oncol. & Tumor Pharmacother. Vol. 8, No. 1, pp. 45–47 (1991).) Mr. Crawford had been diagnosed as having Kaposi's Sarcoma incident to human immunodeficiency virus infection, and had been told he had only 2 to 4 weeks left to live. Mr. Crawford was the first patient of Drs. Alonso and Logan, who together with perfasionist Joseph A. Guzman heated his blood to 42° C. which, the doctors said, killed the human immunodeficiency virus. Although NIAID discounted Mr. Crawford's recovery due to an alleged error in diagnosis—NLAMD maintained that Mr. Crawford never had Kaposi's Sarcoma but had cat-scratch fever instead—six other doctors besides Drs. Alonso and Logan had diagnosed Mr. Crawford's skin lesions as Kaposi's Sarcoma and growing numbers of physicians are convinced that hyperthermia provides a proven antiviral protocol. For example, Dr. Robert S. Jenkins, Medical Director of the Immuno Suppressed Unit at Hollywood Community Hospital, believes that the hyperthermia was responsible for curing Mr. Crawford's Kaposi's Sarcoma lesions.

In a completely separate effort from Drs. Alonso and Logan, Dr. Shawn Hankins, a chiropractor in Port Angeles, Wash., has supported hyperthermia treatments since July 1987 (as explained in the Acquired Immunodeficiency Syndrome Treatment News, Issue No. 104, Jun. 1, 1990, p. 2). He points out that human immunodeficiency virus is heat sensitive and, in addition, hyperthermia can cause increased T-cell proliferation, phagocytosis, and increased production of antibodies and interferon. Observations of patient improvement which sometimes follows pneumocystitis (which causes a high fever) also support this conclusion.

Other publications directed generally toward the treating of human inmmunodeficiency virus with heat include: Weatherburn, H., "Hyperthermia . . .," The British Journal of Radiolog Vol. 61, No. 729, pp. 863–864 (1988); Yatvin, M. B., "An Approach. Using Hyperthermia and Membrane Modification," Medical Hvpotheses, Vol. 27, pp. 163–165 (1988); and U.S. Pat. No. 4,950,225 to Davidner et al., "Method for Extracorporeal Blood Shear Treatment."

The latter, Davidner et al., discusses the extracorporeal treatment of the blood of a human immunodeficiency virus patient with a) hyperthermia; b) mechanical shear and/or c) irradiation. When hyperthermia is used, the blood is heated to between 41.00 and 42.5° C. (or somewhat higher), and pH is adjusted by oxygenating the blood with an extracorporeal oxygenator and by adding sodium bicarbonate intravenously when necessary. Blood is held under low flow or static conditions, extracorporeally, so that the blood treatment or treatments are (assertedly) maximally successful in ineffectuating the human irumunodeficiency virus.

U.S. Pats. No. 5,354,277 and No.5,476,444 are directed to methods and apparatus for effecting whole-body hyperthermia, but even these designs may be improved by incorporating fluid handling systems in which the temperature of the fluid can be controlled more easily, in which the risk of contamination is minimized, and in which the design of the fluid handling system is optimized for a particular indication. A need therefore exists for disposable fluid handling systems with specialized configurations.

SUMMARY OF THE INVENTION

The present invention is a method and device for extracorporeal treatment of a patient by heating the patient's blood and/or a regional anatomic area which utilizes an optional hemodialysis machine capable of heating the fluids to 48° C., an optional parallel plate dialyzer together with a sorbent-based detoxifier, a tubular heat exchanger and a high flow positive displacement pump-in addition to various probes and catheters. The present invention is further a method and device for circulating heated perfusion fluid within a body cavity of a patient utilizing a heat exchanger, heater and high flow positive displacement pump in addition to various catheters, fluid sets and sensors. The present invention also includes a disposable tubing set for directing fluids used in extracorporeal hyperthermia procedures. The tubing set contains a fluid reservoir, accommodates the positive displacement pump, and includes a heat exchanger for heating blood or fluid. The specific improvements in extracorporeal heating afforded by this w system inhere in the combined high flow of the pump and the high temperature-up to 52° C.—achievable in the heat exchanger to achieve fast heating of the perfusion fluid to a temperature sufficient so that at the time such fluid enters the body cavity of the patient the perfusion fluid is at least 41° C. up to 48° C., and preferably about 430° C. to 45° C., which together provide unprecedented speed and efficiency in the administration of hyperthermia treatments in extracorporeal blood or circuits. Computer controlled alarms provide enhanced safety monitoring. The prepackaged blood or sterilized fluid handling system enhances safety and may be configured to respond to a particular indication.

DETAILED DESCRIPTION OF THE INVENTION

Figure 1:
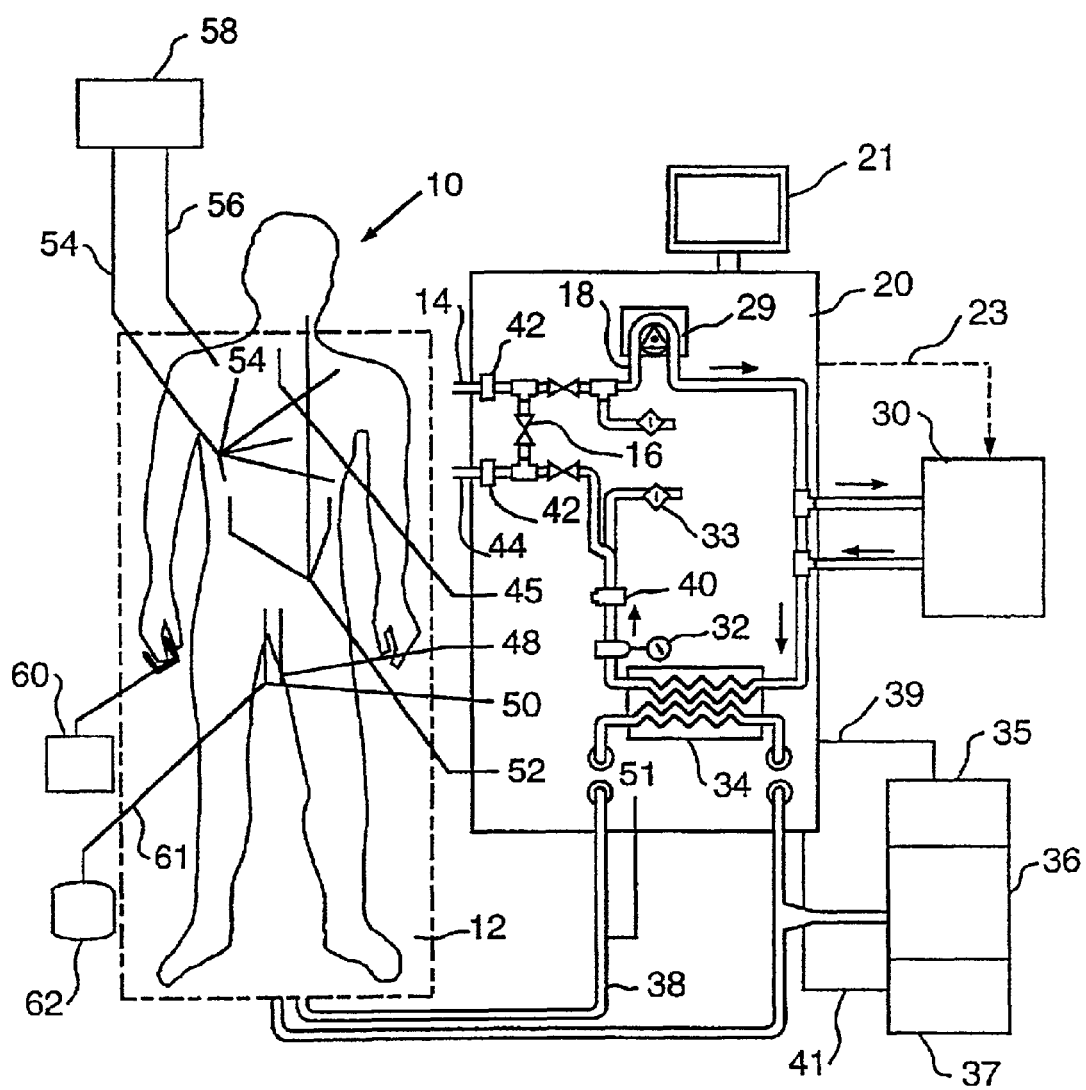
FIG. 1 is a schematic representation of the hyperthermia apparatus.

The present invention includes a method and device for extracorporeal treatment of a patient by heating the patient's blood and/or a regional anatomic area which utilizes an optional hemodialysis machine capable of heating the fluids to 48° C., an optional parallel plate dialyzer together with a sorbent-based detoxifier, a tubular heat exchanger and a high flow positive displacement pump-in addition to various probes and catheters. A specific improvement in extracorporeal heating afforded by this system inheres in the combined high flow of the positive displacement pump and the high temperature—up to 52° C.—achievable in the heat exchanger to achieve fast heating of the perfusion fluid to a temperature sufficient so that at the time such fluid enters the body cavity of the patient the perfusion fluid is at least 41° C. up to 48° C., and preferably about 43° C. to 45° C., which together provides unprecedented speed and efficiency in the administration of hyperthermia.

One of the present blood-specific techniques, which makes use of certain optional equipment, can be summarized as follows. After amnesics and analgesics or other sedation (not necessarily general anesthesia) are given to the patient, two catheters are placed —by catheter placement techniques known in the art including local anesthesia—in the jugular, subclavian or femoral vein or arteries (whichever is most accessible for any given patient). Heparinization is effected only upon initial catheterization at a level of approximately 1.5 to 3 mg./kg. per kilogram patient body weight. In the process of whole body perfusion induced hyperthermia, a charcoal-based sorbent hemodialyzer is optionally connected to the extracorporeal blood "circuit"; the circuit also contains an optional parallel plate dialyzer together with a cbarcoal-based sorbent detoxifier. The desired core body temperature of about 420° C. (4142.5° C., more preferably 41.542° C.) is reached in about 20 to 50 minutes. This elevated body temperature is maintained for 2 hours, and cooling is subsequently effected over a period of 20 to 40 minutes. During the procedure, the patient is monitored for pulmonary artery pressure, radial artery pressure and pulmonary artery and bladder temperature. After 2 hours, the patient is cooled to between 38° and 39° C. and extracorporeal blood circulation is ended.

For this blood treating application, after placement of the catheters, the blood flows through 1) a high-flow positive displacement pump capable of pumping up to 2400 ml/minute of the patient's blood; 2) a tubular heat exchanger and 3) a stopcock for collecting and/or monitoring the extracorporeal blood, prior to return of circulation through the return catheter. In addition an optional charcoal-based sorbent hemodialysis machine containing a parallel plate dialyzer can be added; an exemplary hemodialysis machine is the A2008DJ 8E, manufactured by Fresenius, USA. Hollow-fiber, high flux dialyzers are well known in the art, but one among the many available is the F80 dialyzer, also available from Fresenius, USA. A suitable tubular heat exchanger is available from Bard Inc. (Bard Cardioplegia heat exchanger). Additional features include a temperature probe, pressure sensors and automatic visual and sonic alarms and shutdown valves; safety features including shutdown apparatus and alarms are important in the system described herein, because the high (52° C.) temperature of the fluid in the heat exchanger and the high rate of flow (up to 2400 ml/minute) of the positive displacement pump create the possibility of rapid overheating of the patient without shut-off and alarm provisions.

All of the above equipment is well known in the art and only minor modifications are required prior to its use in the present process. The innovative aspect of the system inheres in its overall design and coordinated operation, not in its individual components. The hemodialysis machine is modified by means known in the art to allow the temperature of the dialyzing fluid to be maintained at 48° C. The rapidity of patient heating and cooling is accomplished in part by the elevated temperature of the dialyzing fluid but primarily by the tubular heat exchanger, which in addition to its capacity to maintain its heat exchange fluids at 52° C. is also equipped with a 1200 watt cooler (or an equivalent cooler), to provide for rapid control of blood heating and cooling as the practitioner directs. The heater/cooler and associated equipment, for instance, from Cincinnati SubZero Products, Inc., is modified to allow for water temperatures up to 52° C.

The safety features more particularly include primary and secondary alarms for monitoring the primary fluid temperature in the heat exchanger. At 53.0+/0.5° C, the heating element becomes disabled and an audible and a visual alarm are both activated. At 55+/ −1.7° C. the heater associated with the heat exchanger and the positive displacement pump are both disabled and an audible and a visual alarm are both activated. The system is also equipped to provide bubble detection on the inflow and the outflow of the extracorporeal blood circuit. Bubble alarms are provided and bubble alarm activation occurs upon detection of cumulative 20 μl of bubbles in either the inflow or outflow bubble detector. The system also includes pressure detection sensors on the inflow and the outflow sides of the pump. The inflow pressure range is −500 to +200 mm of Hg (with an alert point of −350 mm of Hg) and the outflow pressure range is −100 to +500 mg of Hg (with an alert point of 450 mm of Hg); visual and audible alarms are provided to inform the operator when blood pressures reach the upper and lower alert points. Secondary fluid temperature monitors and leakage monitors are also provided.

For the purpose of this invention, a "sorbent-based detoxifier" is described as follows but generally encompasses the state-of-the-art of "artificial liver" technology.

Because of the patient's natural depletion of carbohydrate and fat stores, carbohydrates and fats should be administered during and/or after treatment to assure that these precursors are adequately available to what may well be marginally competent metabolic pathways. Hemodialysis maintains levels of phosphate and calcium during treatment—which levels would otherwise fall as a result of the hyperthermia—especially when acid/bicarbonated water is used as the dialyzing solution. Maintenance of arterial oxygen tensions as high as possible during hyperthermia by use of 100% oxygen for ventilation should satisfy the need to maintain greater than normal blood and tissue oxygen tensions necessitated by hyperthermia-increased oxygen consumption.

Blood flow rates range in the area of about 750 ml. per minute to 2400 ml. per minute when human patients are treated as above. When high blood flow and high heat exchanger efficiencies are used, patient target temperature can be accomplished in as little as 20 minutes.

Prior to treatment, patients are screened for underlying heart disease; underlying lung disease (including pulmonary Kaposi's Sarcoma if one or more lesions is greater than a certain size); pregnancy; a Karnofsky score of less than 60%; a non-correctable hematocrit of less than 30 ml.; hemoglobin less than 10%; active opportunistic infection; chemotherapy for any type of cancer 3 or 4 weeks previously; bleeding disorders; or Diabetes Mellitus. Any of the foregoing warrants careful consideration of the risks versus the benefits of hyperthermia treatment, since an important consideration in the practice of the present technique is whether the patient can tolerate it. The prehyperthermia evaluation requires a routine history and physical examination, routine laboratory studies, chest x-rays, urinalysis, electrocardiogram and pulmonary function studies: Special studies include P-24 antigen level assay; reverse transcriptase assay; human immunodeficiency virus cultures; lymphocyte quantitative analysis and thyroid profile.

The present improved hyperthermia technique has application in every indication for which hyperthermia was indicated in the past, namely, to combat neoplasms and viral infections. Human clinical studies have already shown that hyperthermia is effective to treat (not necessarily to cure) viral infections including the retroviral infections such as Hepatitis B and human immunodeficiency viruses. That hyperthermia is effective in all these applications has already been established; the present invention inheres in the improvements to the pre-existing hyperthermia methods and the way in which the improvements to the pre-existing hyperthermia methods and the way in which the improvements create surprising improvements in patient treatment speed and efficiency.

Unlike previously known whole-body hyperthermia techniques, the present protocol is not necessarily conducted using general anesthesia per se but is instead conducted using conscious sedation and/or analgesics. An exemplary analgesic is commercially available as Sublimaze (fentanyl citrate, or N-(1-phenethyl4-piperidyl) propionanilide citrate), a synthetic narcotic analgesic. An exemplary conscious sedation-inducing drug is Propofol, which is a sedative (or hypnotic agent) widely used in outpatient applications. The chemical formula for Propofol is 2,6-diisopropylphenol; the commercial name is Diprivan injection. These drugs are exemplary only, and the invention is not to be considered as limited to these illustrative medications. (However, Versed (midazolam hydrochloride, or 8-chloro-6-(2-fluorophenyl)-1-methyl4H-imidazol[1,5-a][1,4] benzodiazepine hydrochloride), a short-acting benzodiazepine central nervous system depressant, should NOT be used, and other benzodiazepine derivatives are likewise contraindicated. Midazolam hydrochloride and benzodiazepine derivatives in general are biologically incompatible with hyperthermia: while Versed demonstrates typical pharmacologic activity (including reversibility) during the present procedure, the combination of the hyperthermia with the body biochemistry incident to hyperthermia causes disastrous central nervous system trauma (and possible death) six hours after the procedure is complete. With the patient conscious, or at most sedated, central nervous system activity can readily be monitored during hyperthermia treatment.

The use of the optional hemodialysis machines, and parallel plate dialyzers, as well as the underlying technology of their manufacture, is well known and well established in the medical arts. The various acid- and bicarbonate-containing dialyzing solutions available are also well known; typical commercially available dialyzing solutions are also well known; typical commercially available dialyzing solutions are Centrisol (Cobe) or Renasol (Fresenius). Dialysis technology is itself well understood, and therefore is not being repeated here. The optional incorporation of dialysis into the extracorporeal blood surface is intended to accomplish the same blood "clean up" as ordinary dialysis of a renally compromised patient would—even though the hyperthermia patient would ordinarily have functional kidneys. The optional dialysis procedure allows electrolytes to be regulated (sodium, potassium, phosphate, etc. are all kept at appropriate levels in the blood) and in addition any toxins incidental to viral or neoplasm damage or death are "filtered out." Accomplishing such a result is welt within the skill of those who customarily administer dialysis.

In the context of the above-described system for effecting hyperthermia, the extracorporeal circuit can be used to effect whole- or partial-body hyperthermia and, in fact, the combined improvements of including the high volume positive displacement pump and the high capacity heat exchanger make certain isolated anatomic heating protocols possible for the first time. This development is particularly advantageous in view of another function of patient hyperthermia: hyperthermia can beneficially potentiate (or further activate) certain pharmaceutically active agents such as chemotherapeutic agents, as compared with administration of the same agents at normal patient body temperature. For heat potentiable active agents, when hyperthermia is administered in an anatomically specific way, anatomic specificity of active agent potentiation is also achieved. Selective anatomic potentiation of certain active agents, particularly chemotherapeutic agents; can provide immeasurable improvement in patient care and treatment to any negative effects of either the active agent or the hyperthermia itself One anatomic isolation application of the above-described system includes the isolated treatment of the pelvis or lower extremities in patients suffering from pelvic or lower extremity cancers which cannot be controlled by other means. Hemi-perfusion of the pelvic region or lower extremities in these cases offers the opportunity significantly to increase loco-regional drug dosages and to facilitate localized drug/hyperthermia cytotoxic interactions while minimizing systemic toxicity and morbidity. Isolated perfusion of individual anatomic areas such as a limb is within the skill of a practitioner (using temporary balloon occlusion and other perfusion catheterization techniques known in the art). By using the present system with its high volume positive displacement pump and fast and efficient heating and cooling means an isolated anatomic area can be heated and cooled quickly, without the incidental heating of the remainder of the patient's body which would take place if regional heating required longer periods of time. For example, when an isolated limb is treated with the present system for a 60 minute period, virtually no incidental heating of the rest of the body occurs. This benefit was not heretofore available to practitioners of extracorporeal blood heating of localized anatomic areas.

A representative instance of patient treatment with isolated limb therapy involves patients for whom traditional systemic treatments with chemotherapy and immunotherapy had been ineffective. For example, when a patient has had an extensive thigh melanoma, isolated limb perfusion with hyperthermia and active agent administration using the above-described system can be conducted on the single affected leg. Typical active agents for hyperthermia treatment of melanoma of the thigh include melphalan, tumor necrosis factor, and interferon-gamma.

Limbs are not the only anatomic areas which can be perfused in isolation together with the above-described system. The lung and the liver are organs that are amenable to near complete vascular isolation and are also major repositories of metastatic disease. Isolated perfusion with combined active agent and hyperthermia therapy is feasible using the above-described combined system. A particular therapy for mesothelioma beneficially enhances other treatments by creating perfusion-induced hyperthermia of the chest cavity.

For drug potentiation, the present system may be used advantageously with respect to any active agent whose pharmacologic action (or even bioavailability) is enhanced upon heating. Representative active agents for which beneficial potentiation has been observed upon heating include, but are not limited to, melphalan, mitomycin C and cisplatin. The present system is able selectively to implement hyperthermia-induced drug potentiation of drugs with heat itself is well known and heat potentiable active agents are documented in the patented and published literature.

FIG. 1 illustrates all of the equipment for implementing the above-described blood heating protocols. (Partial or isolated limb hyperthermia is configured the same way except that the perfusionist isolates anatomic areas with blood flow control known in the art.) The patient 10 is positioned on or between optional hyperthermia sources 12, which is a heated water-filled mattress but which may also be a cooled mattress, a heated mattress with heated air emitting blanket, or a related patient temperature controlling means. A blood outflow catheter 14 connects the patient to extracorporeal blood circuit tubing 18. The tubing 18 transports blood from blood outflow catheter 14 to and through an optional sorbent-based hemodialyzer 30 as pumped by a positive displacement pump 29 governed by a computer 20 having a user interface 21 and a communication link 23 between the optional sorbent-based hemodialyzer 30 and the computer 20. The pressure in tubing 18 is monitored by the sensor in communication with the computer 20. After the blood has passed through the optional sorbent-based hemodialyzer, it enters a heat exchanger 34 where it is heated, by heated water originating in the water tank 36 and carried through water lines 38. The water tank 36 typically holds 6 liters of water and is fitted with a beater 35, typically a 1500 watt heater known in the art, and a cooler 37, typically a 1200 watt cooler known in the art, which are in turn communicatively linked with the computer 20 via heater communication line 39 and cooler communication line 41, respectively, and a separate water temperature sensor 51. After the blood is heated (or cooled) in the heat exchanger 34, it passes through temperature gauge 32, a pressure gauge 33 and a blood sample port 40. Air bubbles are detected by the air bubble detectors 42 located near the origin of the outflow catheter 14 and the downstream end of the blood return catheter 44. The blood outflow catheter 14 and blood return catheter 44 may be separate arterial and venous catheters or a single, double-lumen structure, both of which are well known in the art. Regardless of how catheters 14 and 44 are configured, they can be connected by an optional bypass valve 16 to provide the option of immediate return of blood to the patient, should need arise.

The computer 20 provides simultaneous feedback and control of various sensors, gauges and alarms provided within the present system. Patient temperature sensors include the esophageal temperature sensor 45, the rectal temperature sensor 48, and bladder temperature sensor 50. Cardiac output bioimpedance sensors 52 are also provided, along with electrocardiogram leads 54, an arterial pressure sensor 56 and an electrocardiograph/pressure monitor 58. The patient's finger is provided with a pulse oximeter 60 and a bladder catheter 61 connects the bladder to a urine output bag 62. These sensors and the gauges and detectors described above are all interconnected with the computer 20, so that the operator may simultaneously monitor the combined data for all of them. The computer 20 and the user interface 21 are, moreover, configured to provide audible and visible alarms (via the user interface 21) at selectively preset data points from any or all of the gauges and/or detectors. The computer 20 is also able automatically to shut down, for example, the pump 29 and/or the heat exchanger 34 upon communication of certain patient data (as explained above).

When the optional sorbent-based hemodialysis is used, the sorbents clear approximately 50% of the sedative from the bloodstream. Therefore, administration of approximately twice the dosage of sedative will give the same sedative effect as when standard dosage is used.

Figure 2:
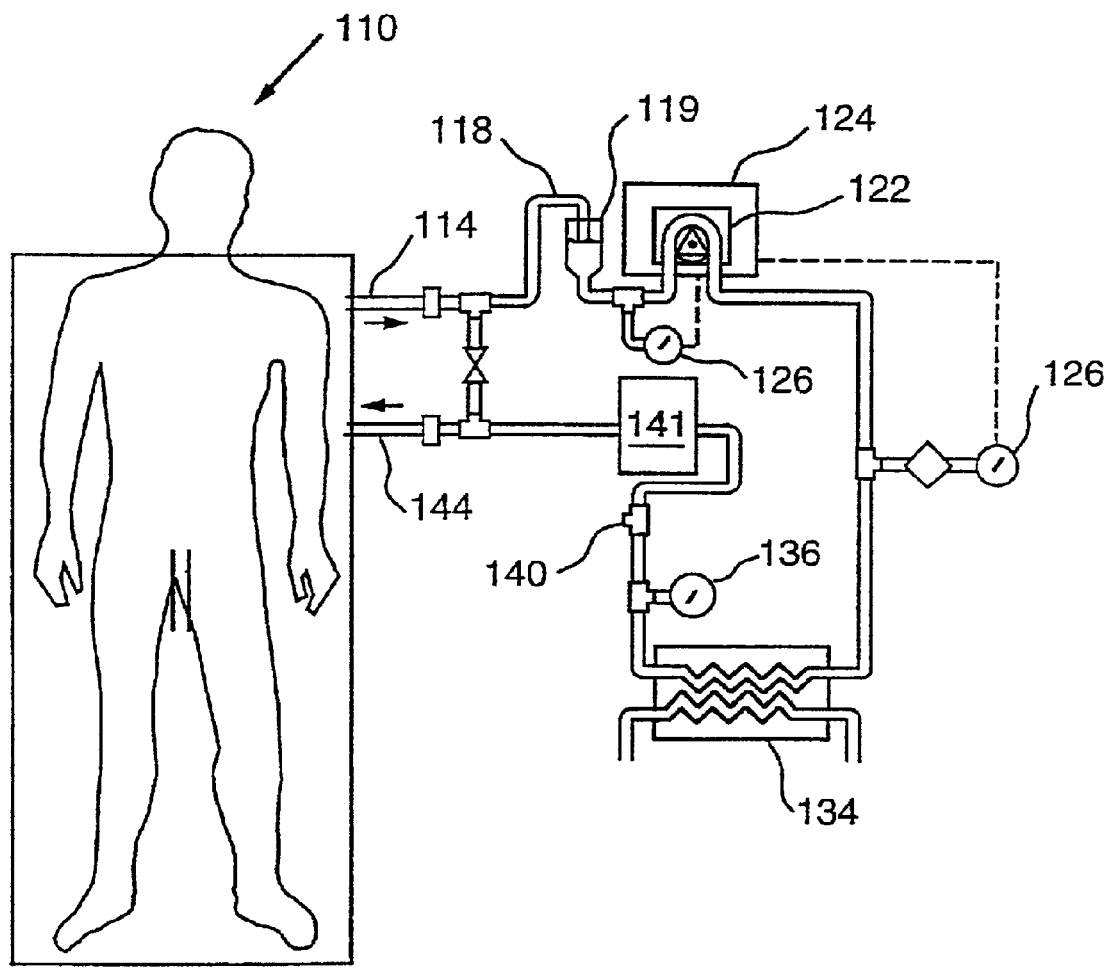
FIG. 2 is a schematic representation of the fluid circuit formed by the disposable tubing set in use.

The present invention may also include a sterile disposable tubing set for directing fluids used in hyperthermia procedures. The tubing set is assembled, sterilized and packaged in sterile packaging prior to use. Sterilization is accomplished by the use of 100% ethylene oxide gas or other appropriate sterilizing agent. In use, the assembled sterile disposable tubing set forms a fluid circuit in conjunction with a portion of a blood system or other volume of an animal or patient, such as the peritoneal cavity, to be perfused. FIG. 2 illustrates the function of the tubing set and cooperating elements as used in connection with the blood system of an animal or patient. Partial or isolated limb hyperthermia is configured the same way except that the treating physician isolates anatomic areas with blood flow control known in the art.

In FIG. 2, a volume to be perfused of a patient or animal 110 is connected by an outflow catheter 114 to extracorporeal tubing 118. The tubing 118 transports fluid, such as blood, from outflow catheter 114 to a fluid reservoir 119 that is part of the disposable tubing set. The fluid in the fluid reservoir acts as a ballast so that the flow rate of the system can be adjusted without introducing air. The fluid then passes through a pump 122 governed by a computer 124. The tubing 118 contains dual Luer port connectors 126; one port on each connector has a pressure tube attached to the tubing 18 and to the device to monitor pre and post roller pump pressure within the tubing 118. The fluid then enters a heat exchanger 134, which is configured to also act as a bubble trap for air bubbles, where it is heated or cooled, by thermal contact with heated or cooled water, to the desired temperature. The temperature of the fluid that is being heated or cooled is monitored by a temperature probe that is directly connected from a port 136 on the heat exchanger to the device. A sample port 140 is connected to the tubing 118 to obtain various samples for laboratory analysis. For certain applications, such as the treatment of isolated limb perfusions for malignant melanoma and sarcomas, the fluid circulating through the system is' blood, and an oxygenator 141 is incorporated into the circuit of tubing 118 to increase the dissolved oxygen concentration in the blood.

Additional devices or features are added to the tubing set for use with specific indications. For example, the interior of the tubing set is coated with a bonded heparin or other bonded coating for the treatment of patients who require low dose heparin or heparinless perfusion, such as patients with post-operative spasms from surgery for subarachnoid hemorrhage, strokes and traumatic brain injury. In addition, the additional Luer port on the Luer connectors 126 can be utilized to accommodate the connection of external devices such as the optional hemodialyzer, or other blood treating devices.

For perfusion of the peritoneum, outflow catheter 114 and return catheter 144 are placed in the peritoneal cavity, and connected to the sterile disposable tubing pack. Sterile secondary solution gravity drains via outflow catheter 114 into fluid reservoir 119, which is an integral part of the sterile disposable tubing pack. The sterile solution used is Lactated Ringer's Solution, U.S.P., or another physiologically compatible solution. Heat is transferred from circulating water of the heater/cooler contained in the device to the secondary solution. The heating of the sterile secondary solution and ultimately the peritoneum results from the heat transfer of the circulating primary fluid in the heat exchanger. The flow rate of the Lactated Ringer's Solution, U.S.P., or other physiologically compatible sterile solution is controlled by the pump. The actual rate of flow is dictated by the return of fluid from the abdomen to the tubing set.

Figure 3:
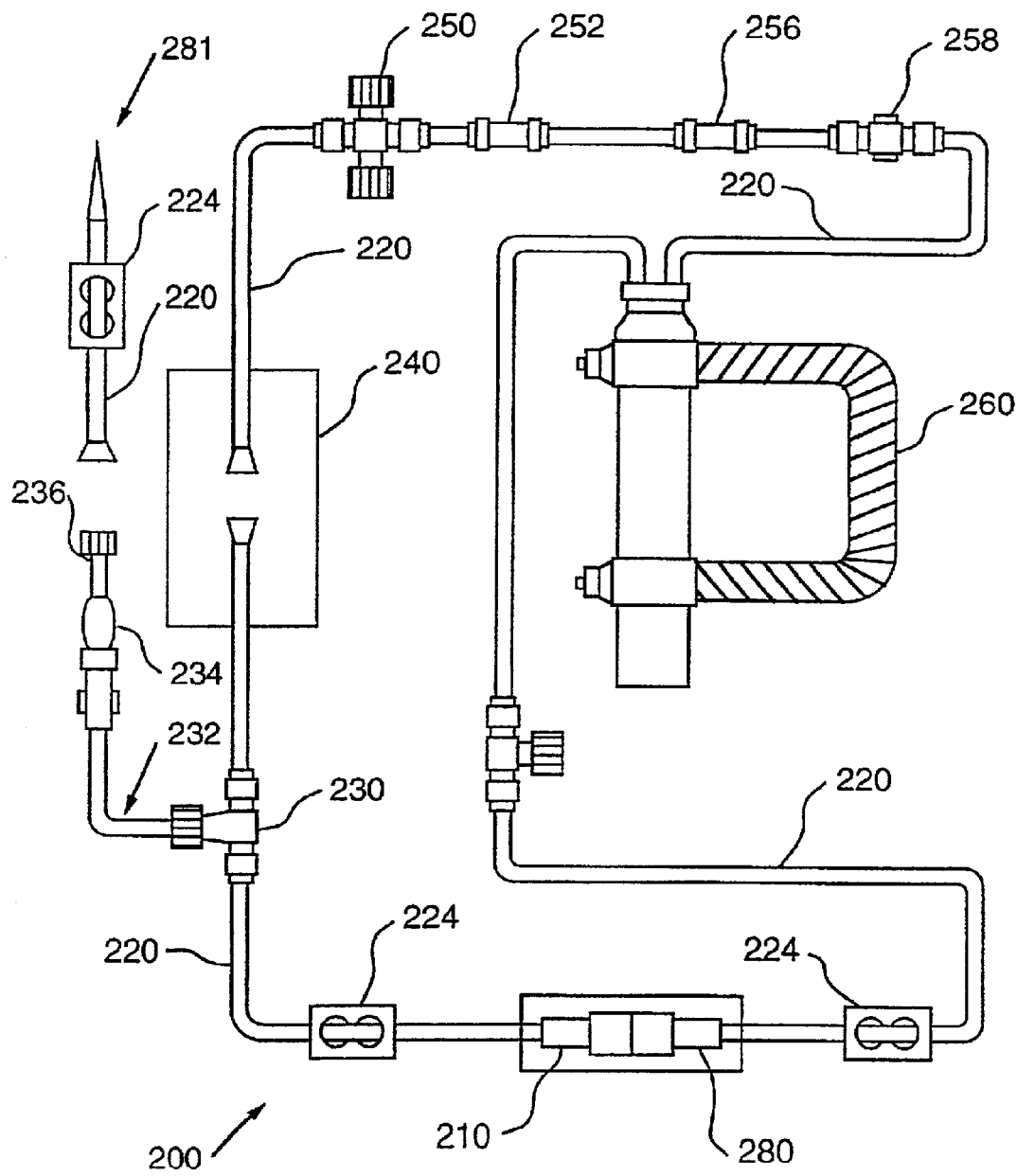
FIG. 3 is a schematic representation of the components of the disposable tubing set.

FIG. 3 illustrates the components of a tubing set 200. Fluid (which can be blood or any other perfusion fluid, such as described above) is withdrawn from the patient or animal through a patient outflow (device inflow) connector 210, which is connected to patient inflow (device outflow) connector 280 and sterilely wrapped until use. Fluid is conducted from connector 210 through tubing 220. Clamps 224 block fluid flow until the tubing set 200 is in use. Fluid passes through a T-connector 230. Bypass 232, containing tubing 220, a one-way stopcock 234 and Luer male non-vented cap 236, enables the sampling of fluid from the patient or animal, should the need arise. A fluid tubing spike 281, containing a clamp 224 and tubing 220, is connected to this bypass to allow the disposable circuit to be fluid filled or "primed" prior to connecting the tubing to a patient or an animal. The tubing spike 281 is typical of the spike used to tap standard intravenous pouches or bags. In normal use of the tubing set 200, fluid flows through tubing 220 that is directly connected to a pouch or flow reservoir 240 which may comprise, for example, a standard cardiotomy tank. Fluid then passes out of the pouch or fluid reservoir via the tubing 120 and the fluid passes through a dual Luer connector 250, a connection reducer 252, a connection reducer 256, and a dual Luer connector 258 and passes into a heat exchanger 260. After heating, the fluid passes out of the heat exchanger through tubing 220 and into the patient via outlet connector 280.

For perfusion involving blood, the tubing kit may be used in conjunction with an exemplary technique as follows. After amnesics and analgesics or other sedation (not necessarily general anesthesia) are given to the patient, two catheters are placed—by catheter placement techniques known in the art including local anesthesia—in thejugular, subclavian or femoral vein or arteries (whichever is most accessible for any given patient). Heparinization is effected only upon initial catheterization at a level of approximately 1.5 to 3 mg./kg. per kilogram patient body weight. In the process of whole body perfusion induced hyperthermia, a charcoal-based sorbent hemodialyzer is connected to the extracorporeal blood "circuit"; the circuit also contains an optional parallel plate dialyzer together with a charcoal-based sorbent detoxifier. The desired core body temperature of about 42° C. (41–42.5° C., more preferably 41.5–42° C.) is reached in about 20 to 50 minutes. This elevated body temperature is maintained for 2 hours, and cooling is subsequently effected over a period of 20 to 40 minutes. During the procedure, the patient is monitored for pulmonary artery pressure, radial artery pressure and pulmonary artery and bladder temperature. After 2 hours, the patient is cooled to between 38° and 39° C. and extracorporeal blood circulation is ended.

More particularly, after placement of the catheters, the blood flows through 1) a high-flow positive displacement pump capable of pumping up to 2400 ml/minute of the patient's blood; 2) a tubular heat exchanger and 3) a stopcock for collecting and/or monitoring the extracorporeal blood, prior to return of circulation through the return catheter. In addition an optional charcoal based sorbent hemodialysis r, machine containing a parallel plate dialyzer can be added; an exemplary hemodialysis 3 machine is the A2008DJ 8E, manufactured by Fresenius, USA. Hollow-fiber, high flux dialyzers are well known in the art, but one among the many available is the F80 dialyzer, also available from Fresenius, USA.

Regardless of whether the tubing system is used with blood or other fluids, a suitable tubular heat exchanger is available from Bard Inc. (Bard Cardioplegia heat exchanger). Additional features include a dual-sensing temperature probe, pressure sensors and automatic visual and sonic alarms and shut-down valves; safety features including shut-down apparatus and alarms are important in the system described herein, because the high (up to 52° C.) temperature of the fluid in the heat exchanger and the high rate of flow (up to 2400 ml/minute) of the positive displacement pump create the possibility of rapid overheating of the blood or fluid without shut-off and alarm provisions.

The invention is further illustrated by means of the following examples.

Example 1

A mesothelioma patient is screened for excessive frailty due to elevated age or excessive prior chemotherapy, severe cachexia, small body mass or a requirement for extensive peritoneal stripping. Following laparotomy, the patient must be stable with active bleeding controlled, and to have had satisfactory tumor debulking. The patient is allowed to cool during laparotomy and cytoreductive surgery. Passive measures include cooling the room temperature, using unwarmed intravenous solutions, and not warming the airway gases. Peritoneal perfusion catheters and temperature probes are placed at this time. For the purpose of this example, catheters are not introduced intravenously but only to and from the peritoneal cavity via the laparotomy incision. Constant temperature monitoring is conducted in the pulmonary artery or esophagus as well as in the inflow and outflow catheter loci. The abdominal incision is temporarily closed. Intraperitoneal hyperthermia begins by establishing a reliable circuit of perfusate to and from the peritoneal cavity, with the perfusate circuit having a volume of about 2 to 3 liters. The perfusate itself may be any suitable fluid including but not limited to standard peritoneal dialysis fluid and preferably contains an initial dose of 30 mg. of mitomycin C. Heating of the perfusate circuit is conducted as though the liquid in the circuit were extracorporeal blood, that is, the system heats the perfusate liquid via the heat exchanger etc., as operated by the perfusionist or other operator. Additional mitomycin C may be added at the discretion of the practitioner. Treatment proceeds for 1 to 2 hours with a 20 to 40 cooling time. Inflow temperatures and outflow temperatures are not permitted to exceed 45° C. and 43°C., respectively, and the patient core temperature is not permitted to exceed 38.5° C. To monitor systemic mitomycin C assimilation, blood, perfusate, and/or urine samples are taken at 15 minute intervals. The peritoneal catheters and probes are removed, wounds and incisions closed, drains and tubes placed, and the patient is transferred to the Intensive tare Unit for at least 24 hours, with clinical follow up thereafter.

Example 2

A pre-operative evaluation of a human immunodeficiency virus infected human patient includes: biopsy of any existing Kaposi's sarcoma lesion; hematic biometry; biochemical profile; electrolytes, antigen P24; reverse transcriptase assay;

western blot; human immunodeficiency virus culture; immunoglobin assay; $CD_4$; phospholipase assay; coagulation studies; interferon assay; interleukine 2 assay; interleukine 2 receptor assay; spirometry; and echocardiogram.

Patients (either male or female) are selected for treatment in this study if they are between the ages of 18 and 40, test positive for the human immunodeficiency virus, and have normal or at least 80% normal pulmonary, cardiac, renal and hepatic functions. (Patients are excluded from this study if they exhibit severe immunodepression, extensive tumoral activity in vital organs (lung, liver, etc.), and are at cardiac risk or have had radiation of the mediastinum or vital organs.)

The whole-body hyperthermia is effected on each human patient as follows.

After an analgesic (see below) is given to the patient, two catheters are placed (under local anesthesia) in the jugular, subclavian or femoral vein (whichever is most accessible for any given patient). Heparinization is effected only upon initial catheterization at a level of approximately 2.4 mg. per kilogram patient body weight. A hemodialyzer capable of increasing the temperature of the dialyzing solution to 48° C. is 3:1 incorporated in the extracorporeal blood "circuit"; the circuit also contains a parallel plate dialyzer, a high volume positive displacement pump and a heat exchanger (52° C. capacity) for rapid control of the temperature. The desired core body temperature of about 42° C. is reached in about 20 to 50 minutes of extracorporeal blood heating. This elevated body temperature is maintained for 2 hours, and cooling is subsequently effected over a period of 20 to 40 minutes. During the procedure, the patient is monitored for pulmonary artery pressure, radial artery pressure and pulmonary artery and bladder temperature, in addition to core temperature. These values are monitored with temperature probes, catheters, and probes known in the art. After 2 hours, the patient is cooled to between 38° and 39° C. and extracorporeal blood circulation is ended.

Hemodialysis maintains levels of phosphate and calcium during treatment, which levels would otherwise fall as a result of the hyperthermia, especially when bicarbonated water is used as the dialyzing solution. Maintenance of arterial oxygen tensions as high as possible during hyperthermia by use of 100% oxygen for ventilation satisfies the need to maintain greater than normal blood and tissue oxygen tensions necessitated by hyperthermia-increased oxygen consumption.

The analgesic used is Sublimaze (fentanyl citrate, or N-(1-phenethyl-4 piperidyl) propionanilide citrate), a synthetic narcotic analgesic. Coadministration of benzodiazepine derivatives is strictly avoided.

The preoperative evaluations listed above are repeated 7, 14, 21 and 28 days after the following hyperthermia treatment is effected.

Although the invention has been described with particularity above, it is to be limited only insofar as it is set forth in the following claims.

What is claimed is:

1. A method for implementing hyperthermia comprising:
    creating a fluid circuit external to an animal or patient for which hyperthermia is indicated with at least one catheter;
    positioning a pump in fluid communication with said at least one catheter;
    pumping said fluid at approximately 2400 ml per minute through a heat exchanger, said heat exchanger having a fluid reservoir for maintaining fluid in the reservoir at approximately 52° C.;
    providing at, least one each of a pressure sensor, a temperature sensor, and an alarm; and
    regulating a desired patient temperature with a computer and user interface means that receives signals from the pressure sensor and the temperature sensor;
    establishing a desired patient temperature in as little as twenty minutes.

2. The method according to claim 1 further including the step of detecting when said alarm is activiated.

3. The method according to claim 2 wherein said heat exchanger is a tubular heat exchanger.

4. The method according to claim 1 further comprising fluidly interconnecting the heat exchanger to a 1500 watt heater and a 1200 watt cooler.

5. The method according to claim 1 further comprising administering at least one potentiable pharmaceutically active agent in conjunction with the hyperthermia thus induced.

6. The method according to claim 1 wherein said catheter is equipped with a bypass valve.

7. A method for implementing hyperthermia comprising:
    creating a first fluid circuit including:
        a supply of a first fluid; and
        a heater for heating a flow of said first fluid to an elevated temperature, wherein said heater establishes the elevated temperature of approximately 52° C.;
    creating a second fluid circuit including:
        an inlet for a flow of a second fluid having a temperature which is lower than the elevated temperature of the first fluid, said inlet being adapted to be placed in fluid communication with a patient;
    placing an outlet for the flow of the second fluid in fluid communication with the subject;
    pumping the first fluid at a flow rate of substantially 2400 ml per minute with a pump; and
    raising the temperature of the second fluid for delivery to the subject by using a heat exchanger in fluid communication with each of the first and second fluid circuits and placing the flow of the first fluid in heat exchange relationship with the flow of the second fluid; and
    regulating the first and second fluid circuits with a control system in order to establish a desired treatment temperature for the patient.

8. The method according to claim 7 further comprising the step of circulating the second fluid, which is a fluid other than blood, into and out of a cavity within the patient to create a hyperthermic state in tissue surfaces within said cavity.

9. The method according to claim 8 wherein said circulating step further comprises providing the second fluid only to an anatomically isolated area.

10. The method according to claim 9 further comprises withdrawing the second fluid before the temperature of the second fluid falls below 42° C.

11. The method according to claim 7 wherein said pumping step further comprises heating primarily only the second fluid in an anatomically isolated area, wherein said second fluid is blood.

12. The method according to claim 7 wherein said heat exchanger is a tubular heat exchanger.

13. The method according to claim 7 further comprising fluidly interconnecting said heat exchanger to a 1500 watt heater and a 1200 watt cooler.

14. The method according to claim 7 further comprising administering at least one potentiable pharmaceutically active agent in conjunction with the hyperthermia thus induced.

* * * * *